US011452857B2

(12) United States Patent
Bihlmaier et al.

(10) Patent No.: US 11,452,857 B2
(45) Date of Patent: Sep. 27, 2022

(54) PERIPHERAL INTRAVENOUS CATHETERS HAVING FLOW DIVERTING FEATURES

(71) Applicant: Becton, Dickinson and Company, Franklin Lakes, NJ (US)

(72) Inventors: Bryan Fred Bihlmaier, Provo, UT (US); Jonathan Karl Burkholz, Salt Lake City, UT (US); Bin Wang, Sandy, UT (US)

(73) Assignee: Beeton, Dickinson and Company, Franklin Lakes, NJ (US)

( * ) Notice: Subject to any disclaimer, the term of this patent is extended or adjusted under 35 U.S.C. 154(b) by 167 days.

(21) Appl. No.: 16/719,658

(22) Filed: Dec. 18, 2019

(65) Prior Publication Data

US 2020/0121911 A1 Apr. 23, 2020

Related U.S. Application Data

(62) Division of application No. 15/716,812, filed on Sep. 27, 2017, now Pat. No. 10,543,354.

(51) Int. Cl.
*A61M 39/22* (2006.01)
*A61M 39/10* (2006.01)
(Continued)

(52) U.S. Cl.
CPC ...... *A61M 39/225* (2013.01); *A61M 25/0097* (2013.01); *A61M 39/00* (2013.01);
(Continued)

(58) Field of Classification Search
CPC ................ A61M 39/225; A61M 39/10; A61M 2039/1072; A61M 2205/0205;
(Continued)

(56) References Cited

U.S. PATENT DOCUMENTS 4,048,995 A * 9/1977 Mittleman ............ A61M 39/04 604/86
4,219,022 A * 8/1980 Genese ............... A61M 5/1408 604/86
(Continued)

FOREIGN PATENT DOCUMENTS

CN 104254361 12/2014
CN 204815139 12/2015
(Continued)

*Primary Examiner* — Amber R Stiles
(74) *Attorney, Agent, or Firm* — Kirton McConkie; Whitney Blair; Kevin Stinger

(57) ABSTRACT

PIVCs with extension sets can include one or more flow diverting features for maximizing the amount of flushing that occurs within the interior of the catheter adapter. These flow diverting features can therefore minimize the amount of residual blood, medicament, or other fluid that may exist within the catheter adapter after the PIVC has been flushed via the extension set. The flow diverting features may be in the form of structural modifications to the side port of the extension set, separate components that are contained within the side port or catheter adapter, integrated components within the side port or catheter adapter, other features or some combination of any of these features.

5 Claims, 8 Drawing Sheets

(51) Int. Cl.

| | |
|---|---|
| ***A61M 39/16*** | (2006.01) |
| ***A61M 39/00*** | (2006.01) |
| ***A61M 25/00*** | (2006.01) |
| *A61M 25/06* | (2006.01) |
| *A61M 39/12* | (2006.01) |

(52) U.S. Cl.
CPC ............ *A61M 39/10* (2013.01); *A61M 39/16* (2013.01); *A61M 39/162* (2013.01); *A61M 25/0606* (2013.01); *A61M 39/12* (2013.01); *A61M 2025/0019* (2013.01); *A61M 2039/0036* (2013.01); *A61M 2039/1072* (2013.01); *A61M 2039/1077* (2013.01); *A61M 2205/0205* (2013.01)

(58) Field of Classification Search
CPC .. A61M 2039/1077; A61M 2025/0019; A61M 2039/0036; A61M 39/00; A61M 39/16; A61M 39/162; A61M 25/0606; A61M 39/12; A61M 25/0097; A61M 25/0023; A61M 25/0043; A61M 25/0662
See application file for complete search history.

(56) References Cited

U.S. PATENT DOCUMENTS

| | | | | |
|---|---|---|---|---|
| 5,417,673 | A * | 5/1995 | Gordon | A61M 39/045 604/537 |
| 8,512,294 | B2 | 8/2013 | Ou-Yang et al. | |
| 8,691,887 | B2 | 4/2014 | Ou-Yang | |
| 8,814,833 | B2 | 8/2014 | Farrell et al. | |
| 8,821,455 | B2 | 9/2014 | Burkholz et al. | |
| 9,308,354 | B2 | 4/2016 | Farrell et al. | |
| 2005/0004534 | A1* | 1/2005 | Lockwood | A61M 1/964 604/304 |
| 2010/0135949 | A1 | 6/2010 | Ou-Yang | |
| 2010/0136209 | A1 | 6/2010 | Ou-Yang et al. | |
| 2015/0231307 | A1 | 8/2015 | Shevgoor et al. | |
| 2016/0089529 | A1* | 3/2016 | Bolz | F16L 13/0209 285/119 |
| 2017/0120033 | A1 | 5/2017 | Kaczorowski | |
| 2018/0304041 | A1* | 10/2018 | Leeflang | A61M 39/0606 |

FOREIGN PATENT DOCUMENTS

| | | |
|---|---|---|
| CN | 208464909 | 2/2019 |
| EP | 0593685 | 4/1994 |
| JP | H1080473 | 3/1998 |
| WO | 94/15665 | 7/1994 |
| WO | 2016/036468 | 3/2016 |
| WO | 2017/074675 | 5/2017 |
| WO | 2017/075507 | 5/2017 |

* cited by examiner

PERIPHERAL INTRAVENOUS CATHETERS HAVING FLOW DIVERTING FEATURES

RELATED APPLICATIONS

This application is a divisional of U.S. patent application Ser. No. 15/716,812, filed Sep. 27, 2017, and entitled PERIPHERAL INTRAVENOUS CATHETERS HAVING FLOW DIVERTING FEATURES, which is incorporated herein in its entirety.

BACKGROUND

A peripheral intravenous catheter (PIVC) is an intravenous device that is designed to be placed into a peripheral vein. A PIVC may oftentimes be configured as a "closed" or "integrated" IV device which refers to the fact that the device is configured to prevent blood from escaping the device during insertion of the catheter. Typically, such PIVCs are designed with an integrated extension set to accomplish this.

FIG. 1 provides an example of a typical PIVC 100 that includes an integrated extension set. PIVC 100 includes a catheter adapter 101 having a distal end from which a catheter 102 extends and a proximal end within which a septum 103 is positioned. Although not shown, PIVC 100 would initially include an insertion needle that would extend from the proximal end of catheter adapter 101, through septum 103, and out through the distal end of catheter 102. Septum 103 functions to seal the interior of catheter adapter 101 after this insertion needle (or any other inserted device) is withdrawn. The extension set of PIVC 100 is formed by a side port 104 which is fluidly coupled to the interior of catheter adapter 101, an extension tube 105, and an adapter 106. Fluid injected into extension tube 105 via adapter 106 will flow into the interior of catheter adapter 101 via side port 104 and ultimately into the patient via catheter 102. In this way, a fluid, such as a medicament, can be administered to the patient without requiring direct access to the interior of catheter adapter 101.

While a PIVC is inserted into a patient's vein, it may be necessary to flush the PIVC. For example, during the insertion of catheter 102, blood may flow proximally through catheter 102 and into the interior of catheter adapter 101. It is typically desirable to flush the blood from catheter adapter 101 to prevent the growth of bacteria or other pathogens. On the other hand, when a medicament is administered through the extension set, some of the medicament will likely remain within catheter adapter 101. Again, it is typically desirable to flush any residual medicament from catheter adapter 101 into the patient. This flushing is typically accomplished by injecting saline into catheter adapter 101 via the extension set.

With existing PIVCs, it is difficult to completely flush catheter adapter 101 by injecting saline through the extension set. For example, due to the angle of side port 104 relative to the longitudinal axis of catheter adapter 101, the saline will flow into catheter adapter 101 in a distal direction towards catheter 102. To accommodate septum 103, the interior of catheter adapter 101 may be elongated in a proximal direction relative to the opening of side port 104. Although there will be some diversion, the primary flow of the saline will be directly between the opening of side port 104 and catheter 102 as represented by the arrows in FIG. 1A. As a result, it is likely that residual blood, medicament, or other fluid that is located in this "proximal elongated region" will not be adequately flushed from catheter adapter 101.

BRIEF SUMMARY OF THE INVENTION

The present invention is generally directed to PIVCs with extension sets where the PIVCs include one or more flow diverting features for maximizing the amount of flushing that occurs within the interior of the catheter adapter. These flow diverting features can therefore minimize the amount of residual blood, medicament, or other fluid that may exist within the catheter adapter after the PIVC has been flushed via the extension set. The flow diverting features may be in the form of structural modifications to the side port of the extension set, separate components that are contained within the side port or catheter adapter, integrated components within the side port or catheter adapter, or other features.

In one embodiment, the present invention is implemented as an IV access device that includes: a catheter adapter having a proximal end and a distal end and a sidewall forming a lumen that extends therebetween; a catheter that extends from the distal end; a side port that extends outwardly from the sidewall of the catheter adapter, the side port being in fluid communication with the lumen of the catheter adapter; and a flow diverting feature configured to divert fluid flowing through the side port and into the lumen in a proximal direction. In some cases, the flow diverting feature may be in the form of at least one of a protrusion from a sidewall of the side port; a diverter that is positioned centrally within an opening of the side port to thereby form a distal channel and a proximal channel around the diverter for fluid flowing from the side port and into the lumen; a protrusion from a portion of the sidewall of the catheter adapter, the portion of the sidewall being positioned opposite the side port; an insert; or a combination of such features.

In another embodiment, the present invention is implemented as a peripheral intravenous catheter that includes: a catheter adapter having a proximal end and a distal end and a sidewall forming a lumen that extends therebetween; a catheter that extends from the distal end; a side port that extends outwardly from the sidewall of the catheter adapter, the side port being in fluid communication with the lumen of the catheter adapter; and a flow diverting feature configured to divert fluid flowing through the side port and into the lumen in a proximal direction. In some cases, the flow diverting feature may comprise one or more of: a protrusion from a sidewall of the side port; a diverter that is positioned centrally within an opening of the side port to thereby form a distal channel and a proximal channel around the diverter for fluid flowing from the side port and into the lumen; a protrusion from a portion of the sidewall of the catheter adapter, the portion of the sidewall being positioned opposite the side port; or an insert that is positioned within the lumen or within the side port.

In another embodiment, the present invention is implemented as an IV access device that includes: a catheter adapter having a proximal end and a distal end and a sidewall forming a lumen that extends therebetween; a catheter that extends from the distal end; a septum positioned within the lumen at the proximal end of the catheter adapter; a side port that extends outwardly from the sidewall of the catheter adapter, the side port being in fluid communication with the lumen of the catheter adapter; and one or more flow diverting features comprising one or more of: a protrusion from a sidewall of the side port; a diverter that is positioned centrally within an opening of the side port to thereby form a distal channel and a proximal channel around the diverter for fluid flowing from the side port and into the lumen; a protrusion from a portion of the sidewall of the catheter adapter, the portion of the sidewall being positioned opposite the side port; or an insert that is positioned within the lumen or within the side port.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

Figure 1:
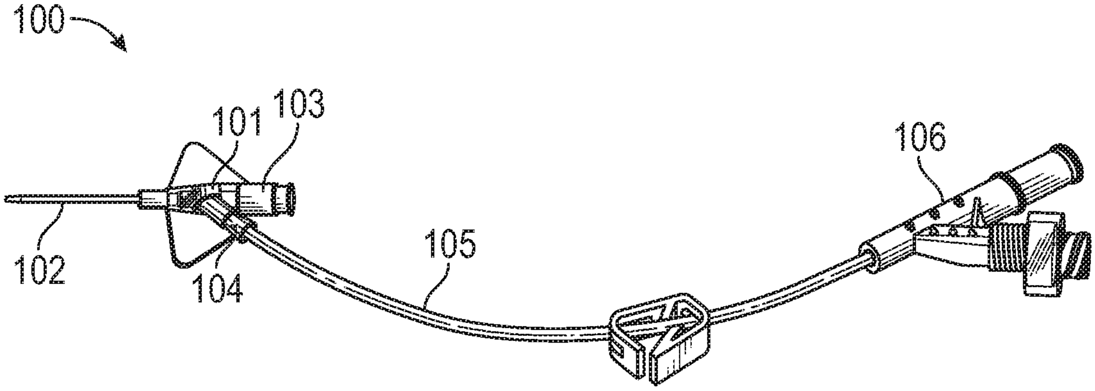
FIG. 1 illustrates a prior art PIVC that includes an extension set.
Figure 1A:
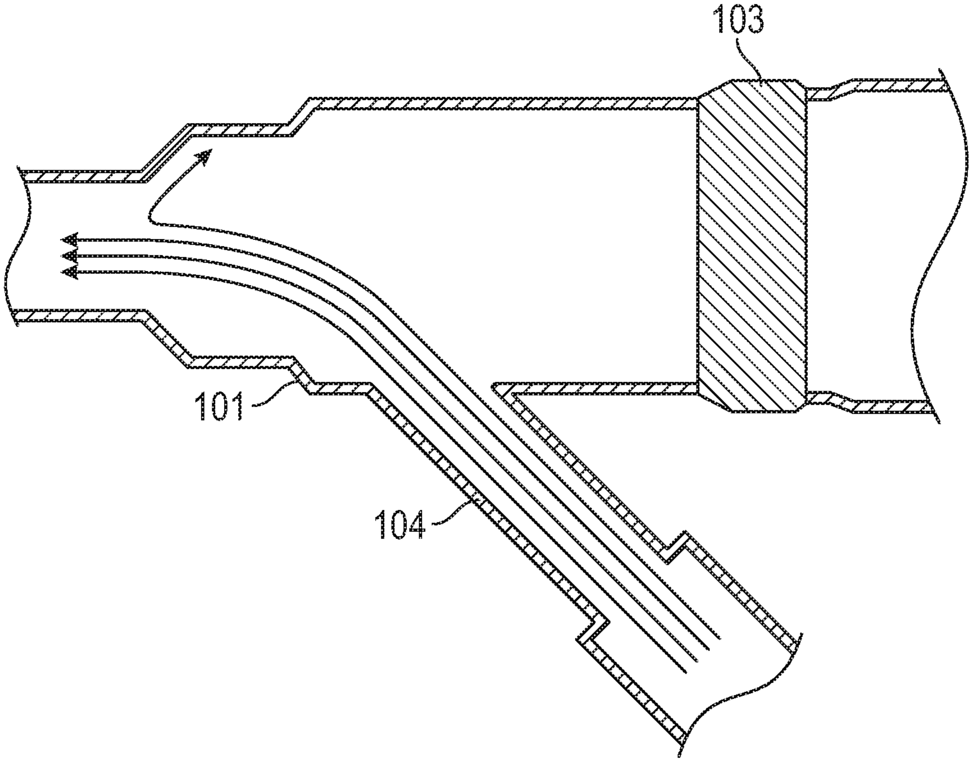
FIG. 1A illustrates how an area of reduced flushing may exist within prior art PIVCs.
Figure 2:
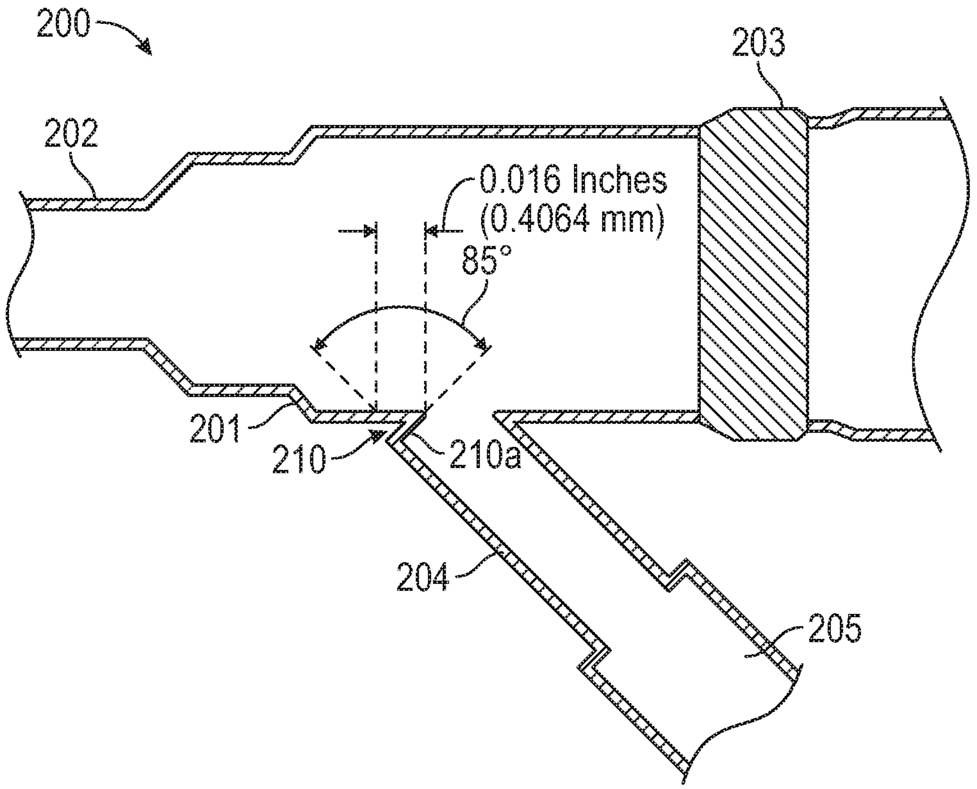
FIG. 2 illustrates a PIVC that includes a flow diverting feature that is integrated into the side port of an extension set.

FIG. 2 illustrates a cross-sectional view of a PIVC 200 that can be configured to include one or more flow diverting features in accordance with embodiments of the present invention. Similar to PIVC 100, PIVC 200 includes a catheter adapter 201, a catheter 202 that extends from a distal end of catheter adapter 201, a septum 203 that is positioned within a proximal end of catheter adapter 201, a side port 204 that extends from a sidewall of catheter adapter 201 and provides a fluid pathway into an interior of catheter adapter 201, and an extension tube 205 that is coupled to side port 204. Although the general structure of PIVC 200 is shown as being similar to the general structure of PIVC 100, this need not be the case. The flow diverting features of the present invention can be incorporated into many different configurations/designs of PIVCs with extension sets.

In FIG. 2, PIVC 200 is configured with a flow diverting feature in the form of a protrusion 210 from the sidewall of side port 204. Protrusion 210 extends into the path of fluid that flows into catheter adapter 201 from the extension set. Two primary characteristics of protrusion 210 are provided in FIG. 2: (1) an angle of the face 210*a* of protrusion 210 relative to the sidewall of side port 204; and (2) a height of protrusion 210. In the embodiment shown in FIG. 2, the angle of face 210*a* is 85° which implies that face 210*a* will be nearly perpendicular to the primary direction of fluid flow into catheter adapter 201. The height of protrusion 201 as depicted is 0.016 inches (0.4064 mm). This height is measured as the distance between the tip of face 210*a* and the point where the axis of the sidewall of side port 204 intersects the sidewall of catheter adapter 201 (i.e., the point where the opening of side port 204 would have started if the side wall did not include protrusion 210). This height therefore defines how far protrusion 210 extends proximally into the opening of side port 204 along the axis of the sidewall of catheter adapter 201.

Variations in the angle and/or height of protrusion 210 can be made to accomplish different levels of flushing with different impacts on the pressure of the flushing fluid. For example, based on simulations, when protrusion 210 has the depicted angle and height, a 57% in flushing efficiency may be obtained relative to PIVC 100 with an increase in pressure of only 0.2 psi. Other variations that have proven to increase the flushing efficiency include a height of 0.012 inches (0.3048 mm) and an angle of 85°, a height of 0.020 inches (0.508 mm) and an angle of 85°, and a height of 0.016 inches (0.4064 mm) and an angle of 60°. These variations are provided as examples only and should not be construed as limiting the invention to any particular dimensions.

Figure 2A:
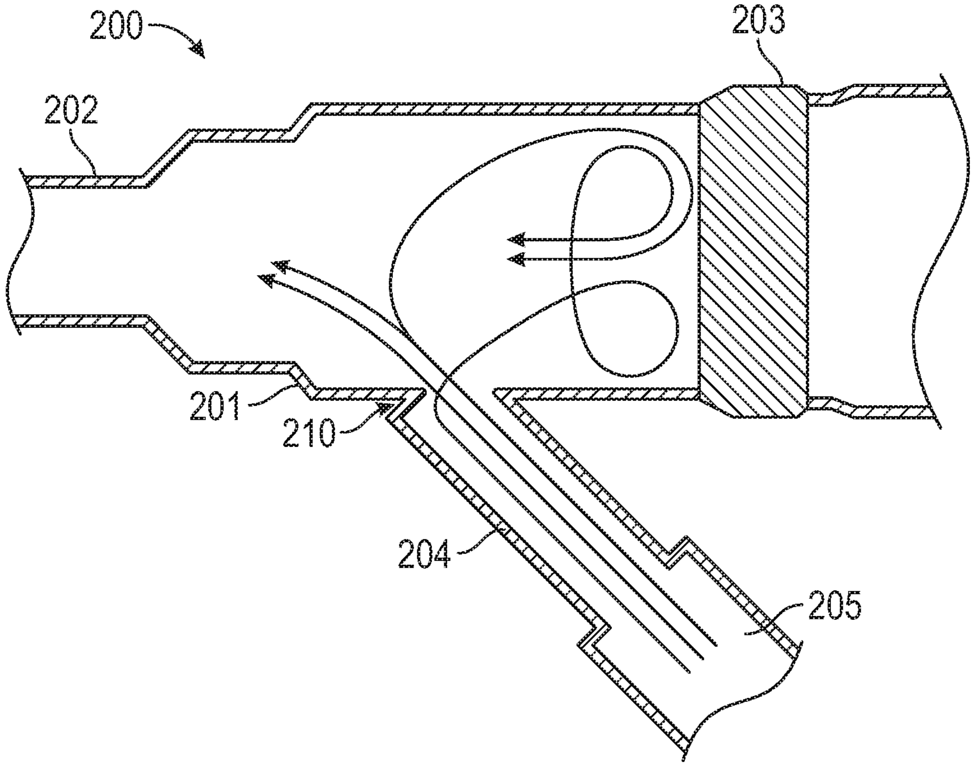
FIG. 2A illustrates how the flow diverting feature of FIG. 2 enhances the flushing of the catheter adapter.

FIG. 2A generally illustrates how protrusion 210 can increase the flushing efficiency of PIVC 200. As represented by the arrows, fluid flowing through side port 204 and into catheter adapter 201 will be diverted by protrusion 210 to create an eddy towards the proximal end of catheter adapter 201. This eddy will minimize the amount of blood, medicament, or other fluid that may remain at the proximal end of catheter adapter 201 after flushing. As mentioned above, this can be accomplished with a relatively trivial increase in the pressure of the flushing fluid (i.e., a trivial increase in force will be required to flush PIVC 200).

Protrusion 210 can be formed in any suitable way. For example, a mold that is used to produce catheter adapter 201 and side port 204 could be modified to form protrusion 210. Alternatively, protrusion 210 could be formed as a separate component that is coupled to side port 204 in any suitable manner. In cases where it is formed as a separate component, protrusion 210 can be formed of a material that is designed to apply antimicrobial benefits to the fluid contained within catheter adapter 201 as will be further described below.

Figure 2B:
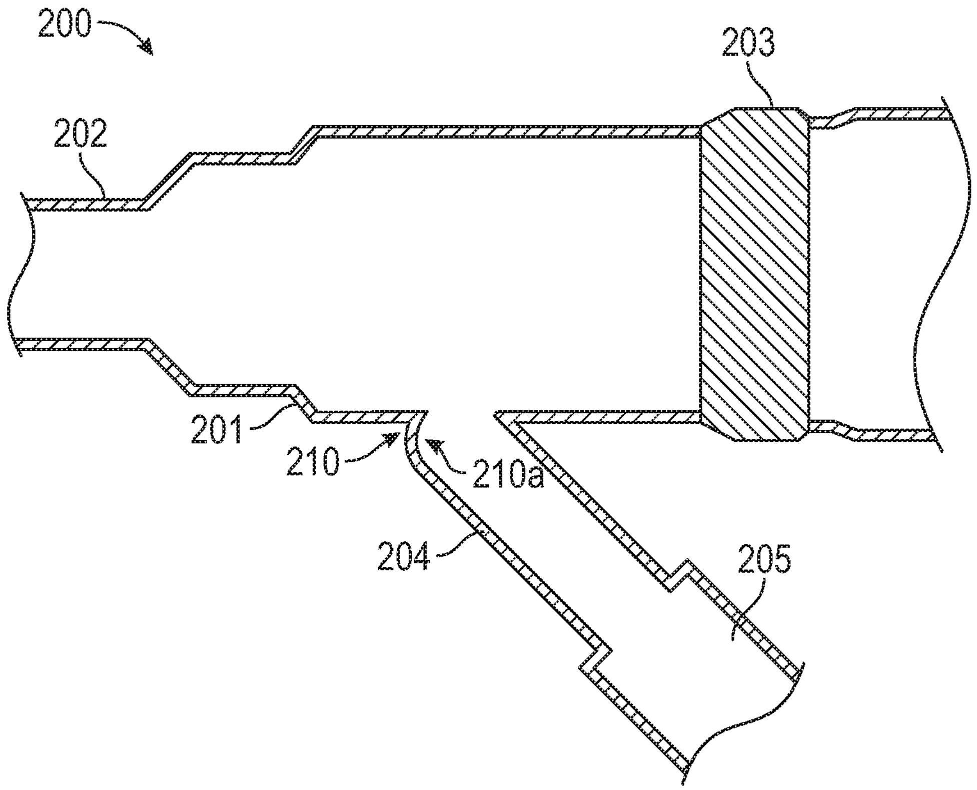
FIG. 2B illustrates a curved embodiment of the flow diverting feature of FIG. 2.

FIG. 2B illustrates an embodiment where protrusion 210 has a curved face 210*a*. In some embodiments, configuring face 210*a* to be curved has resulted in a reduction in the pressure of the flushing fluid and has provided a slight increase in the flushing efficiency. A curved face 210*a* can be employed on any of the above-described variations of protrusion 210 as well as on any other reasonable variation. Although not shown, in some embodiments, face 210*a* can be curved in a spiraling manner. This spiraling can be accomplished by varying the height of protrusion 210 along the various cross-sections. This variation in the height will cause the fluid to be redirected at slightly different angles along the depth of protrusion 210 which in turn can impart a spiraling pattern to the resulting eddy.

Figure 2C:
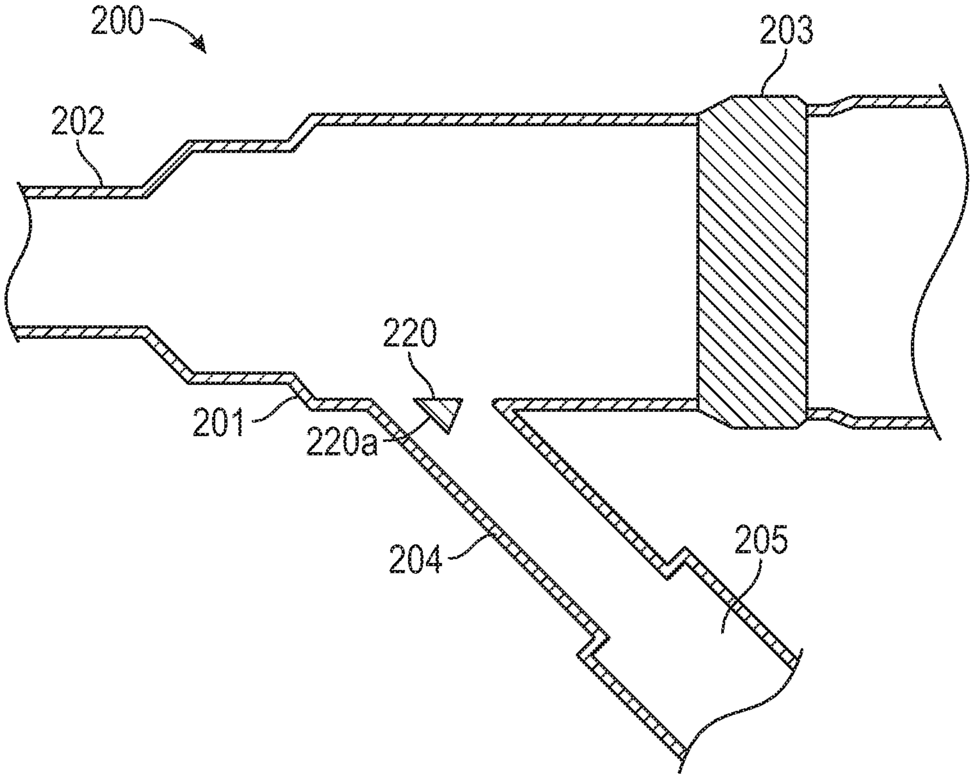
FIG. 2C illustrates how a flow diverting feature can be integrated into the center of the side port.

FIG. 2C illustrates an embodiment where a diverter 220, which has the same general cross-sectional shape as protrusion 210, is positioned centrally within the opening of side port 204. Although not visible in FIG. 2C, diverter 220 could extend between the "upper" and "lower" sidewalls of side port 204 to thereby form fluid channels along the proximal and distal sides of side port 204. As with protrusion 210, diverter 220 has a height and includes a face 220*a* with an angle. Both the height and angle of diverter 220 can be similar to the variations described above for protrusion 210. Simulations have shown that diverter 220 can further improve the flushing efficiencies beyond those obtained with protrusion 210 albeit with an increase in the flushing pressure.

Figure 3A:
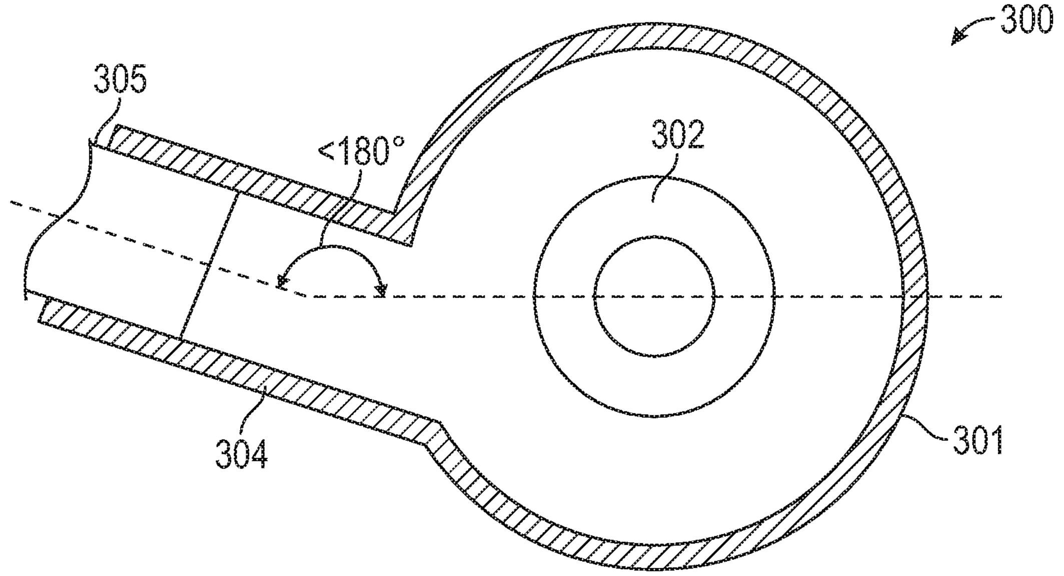
FIG. 3A illustrates a PIVC that includes a side port that has a central axis that is offset relative to the central axis of the catheter adapter.
Figure 3B:
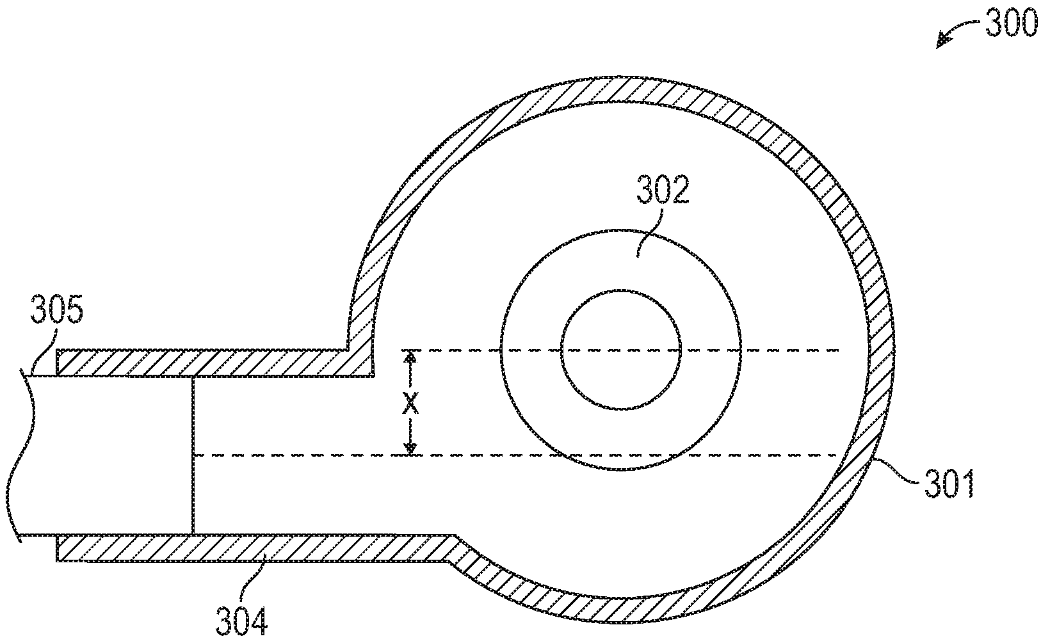
FIG. 3B illustrates a PIVC that includes a side port that has a central axis parallel to but spaced apart from the central axis of the catheter adapter.

FIGS. 3A and 3B each illustrate an embodiment of a PIVC 300 that can have a similar overall structure as the previously described PIVCs. For example, PIVC 300 is shown as including a catheter adapter 301, a catheter 302, a septum (not shown), a side port 304, and an extension tube 305. Unlike the previous figures, FIGS. 3A and 3B are cross-sectional views taken perpendicular to the longitudinal axis of catheter adapter 301 and through side port 304.

In contrast to PIVC 200 where the longitudinal axis of side port 204 was assumed to be in the same plane as the longitudinal axis of catheter adapter 201, the longitudinal axis of side port 304 is either offset relative to the plane of the longitudinal axis of catheter adapter 301 (FIG. 3A) or is parallel to but spaced apart from this plane (FIG. 3B).

More particularly, in FIG. 3A, although the opening of side port 304 is intersected by the plane of the central axis of catheter adapter 301, the central axis of side port 304 is angled downwardly (or upwardly depending on the orientation of the PIVC) relative to this plane (as represented by the less-than 180° angle between the two axes). As a result, fluid flowing into catheter adapter 301 via side port 304 will enter catheter adapter 301 at an angle that deviates from the central axis and will thereby cause the fluid to flow in a swirling or spiraling manner within catheter adapter 301 to increase the flushing efficiency.

A similar swirling or spiraling flow of the flushing fluid can be achieved by configuring side port 304 so that its central axis is substantially parallel with but spaced from the central axis of catheter adapter 301 (by some non-inconsequential distance x) as shown in FIG. 3B. In this way, the opening of side port 304 will be offset towards a bottom (or top depending on the orientation of the PIVC) of catheter adapter 301.

In both embodiments of PIVC 300, the flow of flushing fluid as it exits side port 304 will be directed towards a portion of the sidewall of catheter adapter 301 that is below the central axis. The generally circular shape of catheter adapter 301 will then cause flow to be diverted upwardly in a curving and spiraling manner which will minimize the amount of residual blood, medicament, or other fluid after flushing. In some embodiments, a side port of a PIVC could be configured in accordance with both FIGS. 3A and 3B (i.e., the side port could be angled relative to and offset from the central axis of catheter adapter 301).

Figure 4:
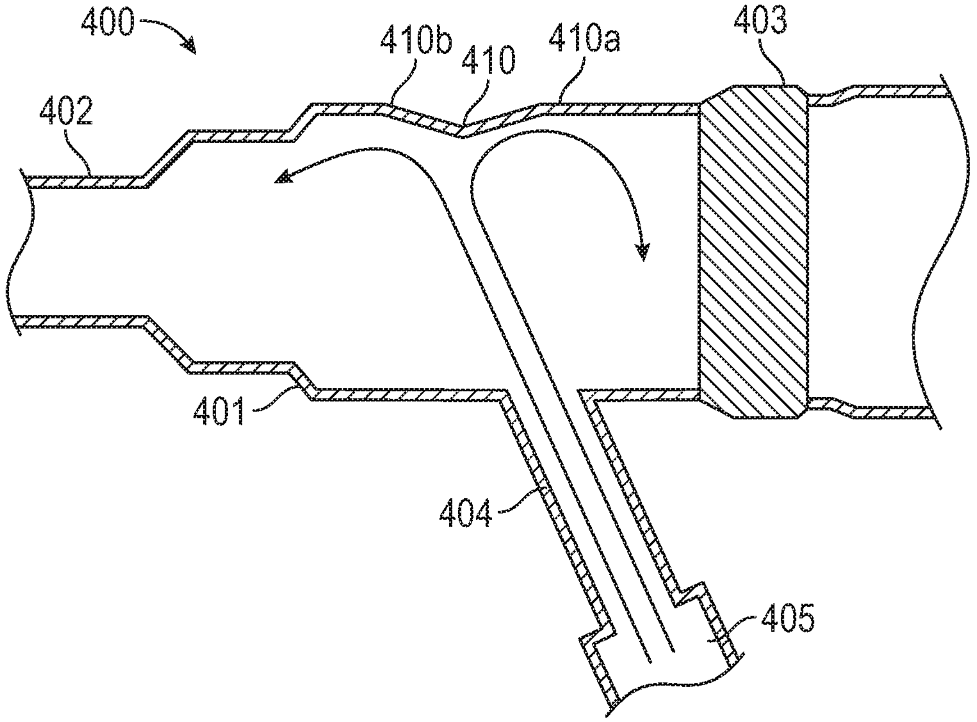
FIG. 4 illustrates a PIVC that includes a flow diverting feature that is positioned on a sidewall of the catheter adapter opposite the side port of the extension set.

FIG. 4 illustrates an embodiment of a PIVC 400 where a flow diverting feature is formed along a sidewall of the catheter adapter opposite the side port. As shown, PIVC 400 includes a catheter adapter 401, a catheter 402, a septum 403, a side port 404, and an extension tube 405 and therefore has a similar general structure as the previously described PIVCs. Additionally, PIVC 400 includes a flow diverting feature in the form of a protrusion 410 from the sidewall of catheter adapter 401. Protrusion 410 can be positioned opposite side port 404 so that fluid flowing out from side port 404 will be incident on protrusion 410. Protrusion 410 can include a proximally directed face 410*a* and a distally directed face 410*b*. Face 410*a* can cause fluid to be diverted in a proximal direction to thereby create an eddy towards the proximal end of catheter adapter 401.

Figure 5A:
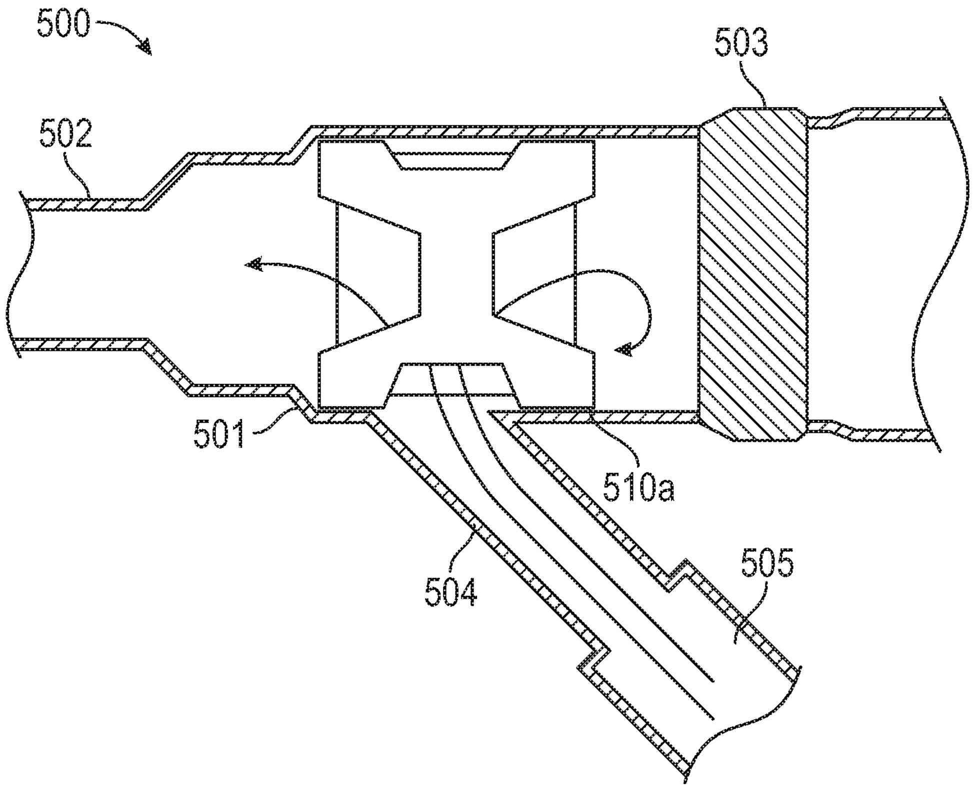
FIG. 5A illustrates a PIVC that includes a flow diverting insert that is positioned within the catheter adapter.
Figure 5B:
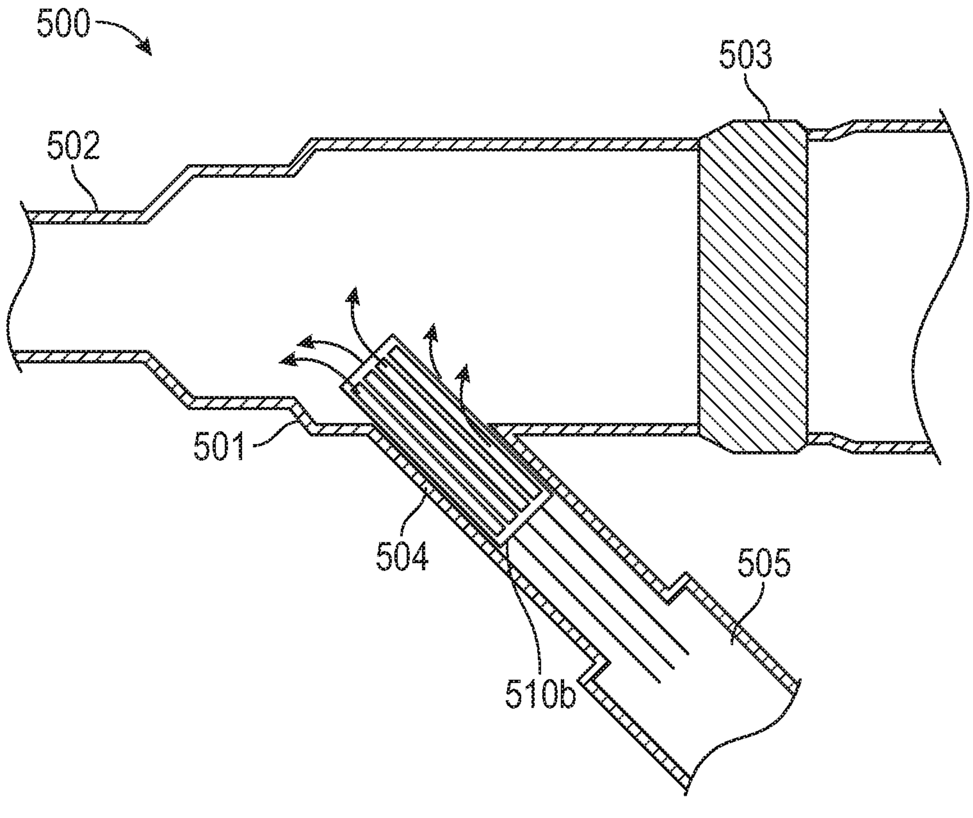
FIG. 5B illustrates a PIVC that includes a flow diverting insert that is positioned within the side port.

FIGS. 5A and 5B each illustrate an embodiment of a PIVC 500 that includes a flow diverting feature in the form of an insert. PIVC 500 includes a catheter adapter 501, a catheter 502, a septum 503, a side port 504, and an extension tube 505. As can be seen, the structure of PIVC 500 itself can be the same as PIVC 100 or any other PIVC that includes an extension set.

In FIG. 5A, PIVC 500 includes an insert 510*a* that is positioned within catheter adapter 501 overtop the opening of side port 504. Insert 510*a* can include a number of openings forming channels through the insert including at least one channel that diverts flow of the flushing fluid in a proximal direction. A suitable insert can be configured with many different shapes, sizes, and orientations of openings to accomplish this diversion.

In FIG. 5B, PIVC 500 includes an insert 510*b* that is positioned inside side port 504 and may extend partially into catheter adapter 501. As with insert 510*a*, insert 510*b* can include a number of openings forming channels for diverting flow of the flushing fluid in a proximal direction. The diversion of flow in the proximal direction can create an eddy to enhance the flushing efficiency as described above.

Figure 6A:
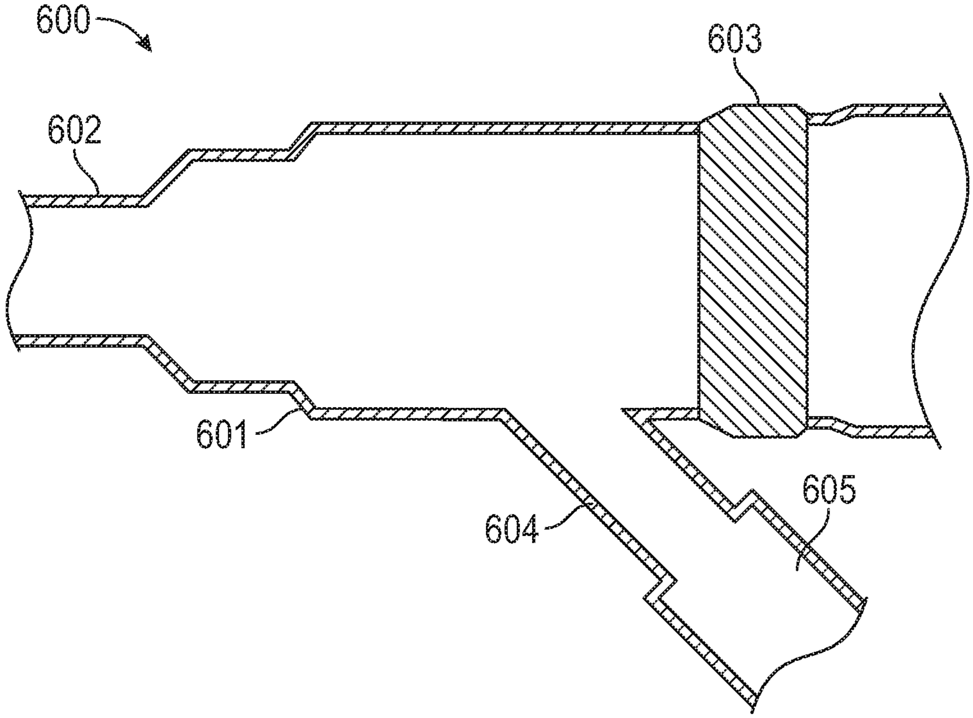
FIGS. 6A and 6B each illustrate a PIVC that includes a side port that is positioned proximate to a septum housed within a proximal end of the catheter adapter.
Figure 6B:
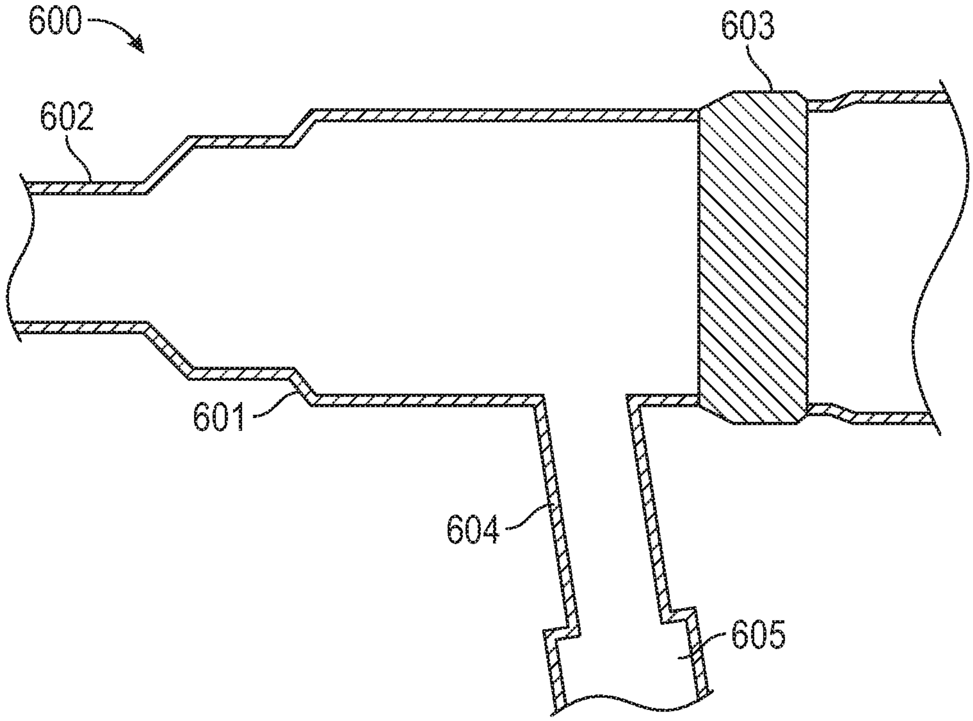

FIGS. 6A and 6B each illustrate how the relative position of the side port along the longitudinal axis of the catheter adapter can be adjusted to further enhance flushing efficiency. Each of these figures depicts a PIVC 600 having a catheter adapter 601, a catheter 602, a septum 603, a side port 604 and an extension tube 605. In FIG. 6A, side port 604 is positioned in a more proximal location proximate septum 603. By positioning side port 604 immediate to septum 603, the area within catheter adapter 601 that is proximal to side port 604 is minimized. By minimizing this area, the eddy and/or proximal diversions provided by the previously described flow diverting features may be more effective. In FIG. 6B, side port 604 is further shown as being oriented at a greater angle relative to catheter adapter 601. In this case, the angle is acute but nearly 90°. With this near 90° angle, the amount by which the flushing fluid will need to be diverted to enhance flushing efficiency is reduced. This is especially true when side port 604 is also positioned proximate to septum 603 as shown in FIG. 6B.

Repositioning of side port 604 to be more proximate to septum 603 and/or adjusting of the angle of side port 604 to be closer to 90° can be performed in conjunction with any of the previously described flow diverting features to enhance their effectiveness. For example, PIVC 600 could also include protrusion 210 or protrusion 410 to cause an eddy to be formed in the proximal end of catheter adapter 601. Due to the limited area of this proximal end, the formation of the eddy during flushing can result in significant improvements in flushing efficiency than were possible in prior art PIVCs. The same would be true by including insert 510*a* or 510*b* in PIVC 600 or by further configuring side port 604 in accordance with FIG. 3A or 3B.

Figure 7:
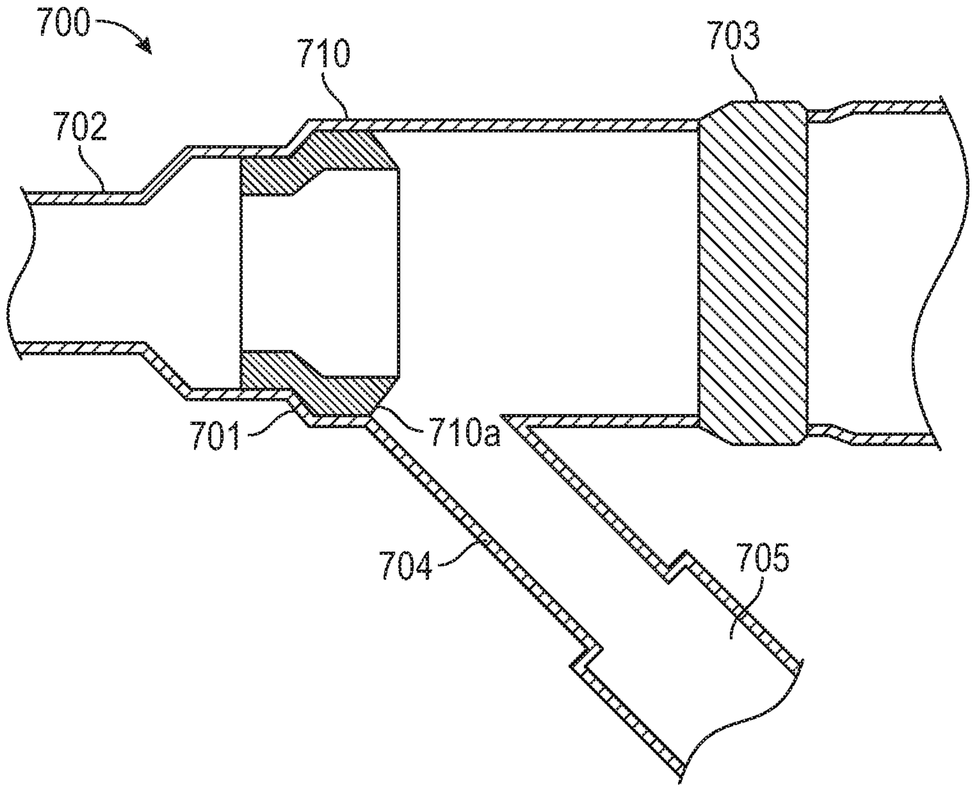
FIG. 7 illustrates a PIVC that includes a flow diverting insert that is positioned within the catheter adapter distal to the side port.
Figure 7A:
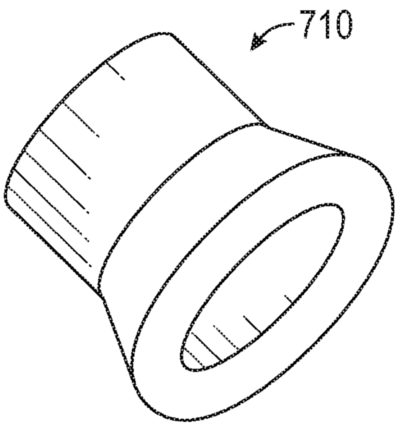
FIG. 7A illustrates a detailed perspective view of the flow diverting insert shown in FIG. 7.

FIG. 7 illustrates a PIVC 700 having a catheter adapter 701, a catheter 702, a septum 703, a side port 704 and an extension tube 705. PIVC 700 also includes a flow diverting feature in the form of an insert 710 that is positioned distal to side port 704. As shown, insert 701 can have a generally annular shape (see FIG. 7A) and can be configured to fit snuggly within the sidewalls of catheter adapter 701 (e.g., via a compression fit). Insert 710 can include a proximal face 710*a* that is oriented outwardly and that extends proximally overtop the opening of side port 704. Face 710*a* can therefore function in a similar manner as protrusion 210 to divert flow of the flushing fluid in a proximal direction.

In some embodiments, inserts 510 and 710 can be formed of a material that provides antimicrobial benefits within the catheter adapter. For example, inserts 510 or 710 could be formed of or coated with a material that elutes an antimicrobial agent such as chlorhexidine. In some embodiments, these inserts could be formed primarily of a hydroscopic material that will swell when wetted to prevent dislodgment.

Although the various flow diverting features have been primarily described as being implemented separately on a PIVC, a combination of two or more of the described features could be employed on a single PIVC. Also, the described flow diverting features can be employed on any type or configuration of a PIVC that includes an extension set (i.e., on any PIVC that has a side port that is used for flushing). Further, although the description has been limited to PIVCs, the flow diverting features can be employed on any other IV access device that includes a side port.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An IV access device comprising:

a catheter adapter having a proximal end and a distal end and a sidewall forming a lumen that extends therebetween;

a catheter that extends from the distal end;

a side port that extends outwardly from the sidewall of the catheter adapter, the side port being in fluid communication with the lumen of the catheter adapter; and a flow diverting feature configured to divert fluid flowing through the side port and into the lumen in a proximal direction, wherein the flow diverting feature comprises a diverter that is positioned centrally within an opening of the side port to thereby form a distal channel and a proximal channel around the diverter for fluid flowing from the side port and into the lumen, wherein a cross-section of the diverter comprises a first face aligned with a longitudinal axis of the catheter adapter, a second face proximate the first face and aligned with a longitudinal axis of the side port, and a third face extending between the first face and the second face and angled with respect to the first face and the second face.

2. The IV access device of claim 1, wherein the diverter extends between opposing sides of the side port.

3. The IV access device of claim 1, wherein the first face, the second face, or the third face is curved.

4. The IV access device of claim 1, wherein the diverter has a varying height.

5. The IV access device of claim 1, wherein the first face, the second face, and the third face are each planar.

* * * * *

UNITED STATES PATENT AND TRADEMARK OFFICE

CERTIFICATE OF CORRECTION

| | |
|---|---|
| PATENT NO. | : 11,452,857 B2 |
| APPLICATION NO. | : 16/719658 |
| DATED | : September 27, 2022 |
| INVENTOR(S) | : Bryan Fred Bihlmaier, Jonathan Karl Burkholz and Bin Wang |

It is certified that error appears in the above-identified patent and that said Letters Patent is hereby corrected as shown below:

On the Title Page

Item (73)
Please change the Assignee information from "Beeton, Dickinson and Company" to read "Becton, Dickinson and Company."

Signed and Sealed this
Thirteenth Day of December, 2022

Katherine Kelly Vidal

Katherine Kelly Vidal
*Director of the United States Patent and Trademark Office*